United States Patent [19]

Porter et al.

[11] Patent Number: 5,254,125
[45] Date of Patent: Oct. 19, 1993

[54] SCROTUM INCISOR INSTRUMENT

[76] Inventors: Wayne Porter, Rte. 1; Jim Reid, 1502 Matthews, both of Bowie, Tex. 76230

[21] Appl. No.: 991,842

[22] Filed: Dec. 16, 1992

[51] Int. Cl.$^5$ .............................................. A61B 19/00
[52] U.S. Cl. ...................................... 606/135; 606/1; 606/167; 606/170; 606/205
[58] Field of Search .................... 128/749, 751; 606/1, 606/39, 45, 51, 52, 107, 110, 118, 125, 135, 137, 139, 140, 142, 144, 165, 166, 167, 170, 171, 172, 174, 175, 177, 181, 182, 183, 205–208, 210, 211; 30/124

[56] References Cited

U.S. PATENT DOCUMENTS

| | | |
|---|---|---|
| 650,496 | 5/1900 | Stohlmann et al. .................. 606/110 |
| 929,833 | 8/1909 | Combs .................................. 606/110 |
| 2,447,169 | 8/1948 | Sousa ..................................... 606/45 |
| 3,006,344 | 10/1961 | Vogelfanger . |
| 3,675,688 | 7/1972 | Bryan et al. . |
| 4,026,294 | 5/1977 | Mattler . |
| 4,572,181 | 2/1986 | Mattler . |
| 4,648,401 | 3/1987 | Mattson . |
| 4,667,671 | 5/1987 | Danzig . |
| 4,691,704 | 9/1987 | Wadsworth . |
| 4,870,965 | 10/1989 | Jahanger . |
| 5,201,739 | 4/1993 | Semm ................................... 606/110 |

Primary Examiner—Stephen C. Pellegrino
Assistant Examiner—Glenn Dawson
Attorney, Agent, or Firm—Dunlap, Codding & Lee

[57] ABSTRACT

An instrument for grasping and incising the scrotum of an animal. The instrument has a barrel, a spring-loaded rod within the barrel, a pair of forceps members attached to the rod and a knife housing with a spring-loaded knife at the forward end of the barrel. A spring-biased latch member is provided to hold the knife in a cocked position. A trigger is attached to the barrel to cock the rod in a forward position with the forceps members extending forward through the knife housing and to release the rod for rapid movement rearward in the barrel. With the knife and rod cocked, the forceps members are applied to the scrotum of an animal. The trigger is then pressed to release the rod and forceps members rearward. The rearward movement of the forceps members draws a portion of the scrotum into the knife housing behind the knife. The final rearward movement of the rod causes the latch member to be tripped, and the knife is released to incise the scrotum.

21 Claims, 4 Drawing Sheets

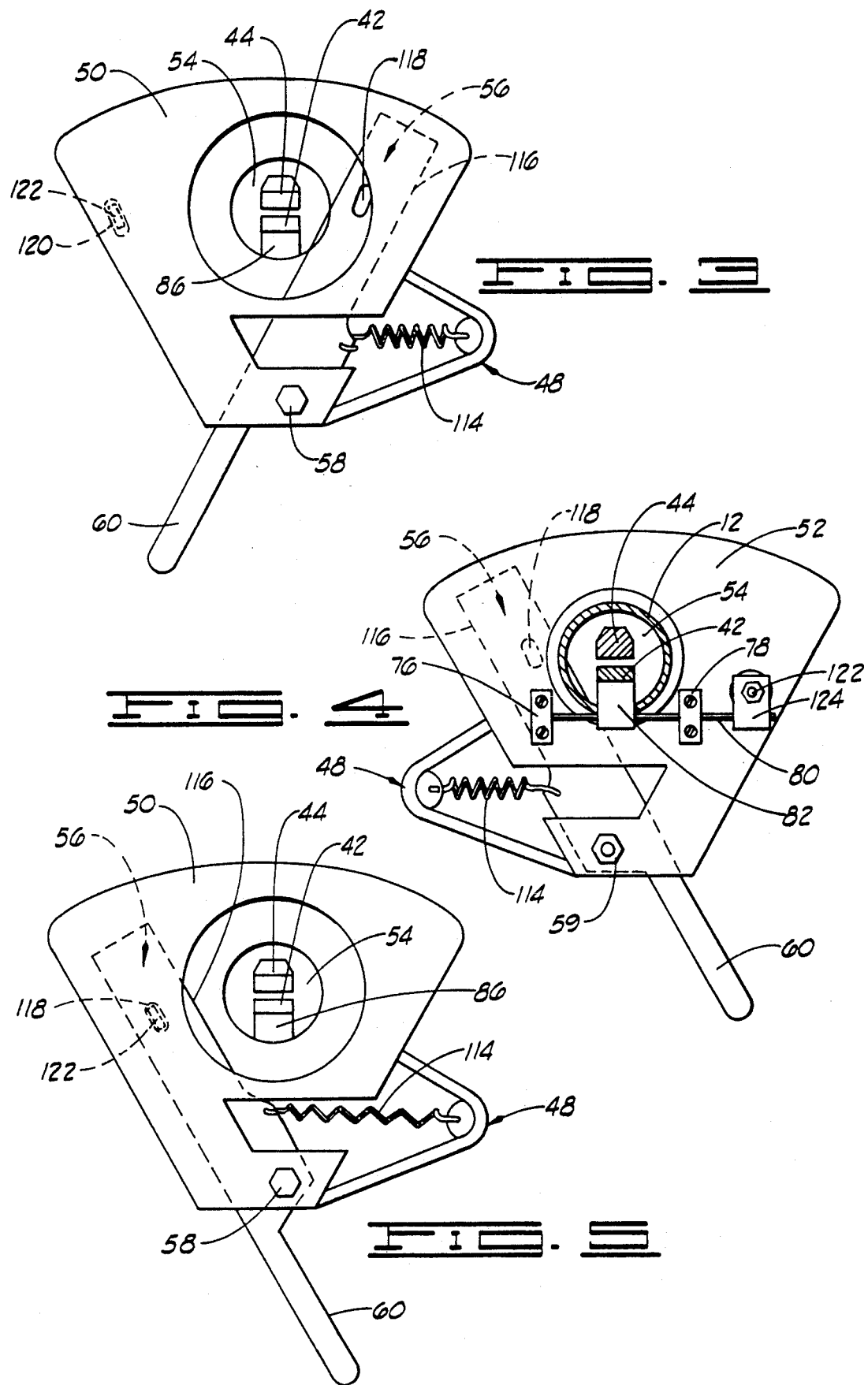

SCROTUM INCISOR INSTRUMENT

BACKGROUND OF THE INVENTION

1. Field of the Invention

The present invention relates to veterinary instruments, and particularly to a veterinary instrument for grasping the scrotum of an animal and incising the scrotum to allow access to the vessels inside the scrotum.

2. Description of Related Art

Castration of a bull calf typically begins with cutting open the scrotum of the bull calf to gain access to the vessels inside the scrotum The incision of the scrotum of the bull calf is usually performed with an open blade. The use of an open blade on a struggling animal weighing several hundred pounds presents a very real danger of injury to the calf and the handler of the open blade.

SUMMARY OF THE INVENTION

The present invention is an instrument for grasping and incising the scrotum of an animal without risk of injury from an open blade.

The instrument comprises a barrel, a spring-loaded rod disposed within the barrel, a pair of forceps members attached to the rod, and a knife housing with a pivot-mounted, spring-loaded knife. The knife housing includes a latch member which holds the knife in a cocked position and releases the knife in response to complete rearward movement of the forceps members. The instrument includes a trigger which pivots to hold the rod and forceps members in a forward, cocked position and to release the rod and forceps members for rapid rearward movement. A forceps lever is provided to open the forceps members and to close the forceps members on a portion of the scrotum of the animal.

An object of the present invention is to provide an instrument which incises the scrotum of an animal while protecting the handler of the instrument from sharp cutting edges.

Another object of the present invention is to provide an instrument which incises the scrotum of an animal quickly and efficiently in order to lessen exposure of the handler to injury by a struggling animal.

Yet another object of the present invention is to provide an instrument which is easy to clean and allows removal of the knife for cleaning, sharpening and replacement.

Other advantages and features of the present invention are apparent from the following detailed description when read in conjunction with the accompanying drawings and appended claims.

BRIEF DESCRIPTION OF THE DRAWINGS

FIG. 3 is a forward end elevation of the instrument of FIG. 1 with the knife in the released position.

FIG. 4 is a cross-sectional view of the instrument along the lines 4—4 of FIG. 1.

FIG. 5 is a forward end elevation of the instrument of FIG. 1 with the knife in the cocked position.

DETAILED DESCRIPTION OF THE PREFERRED EMBODIMENTS

Figure 1:
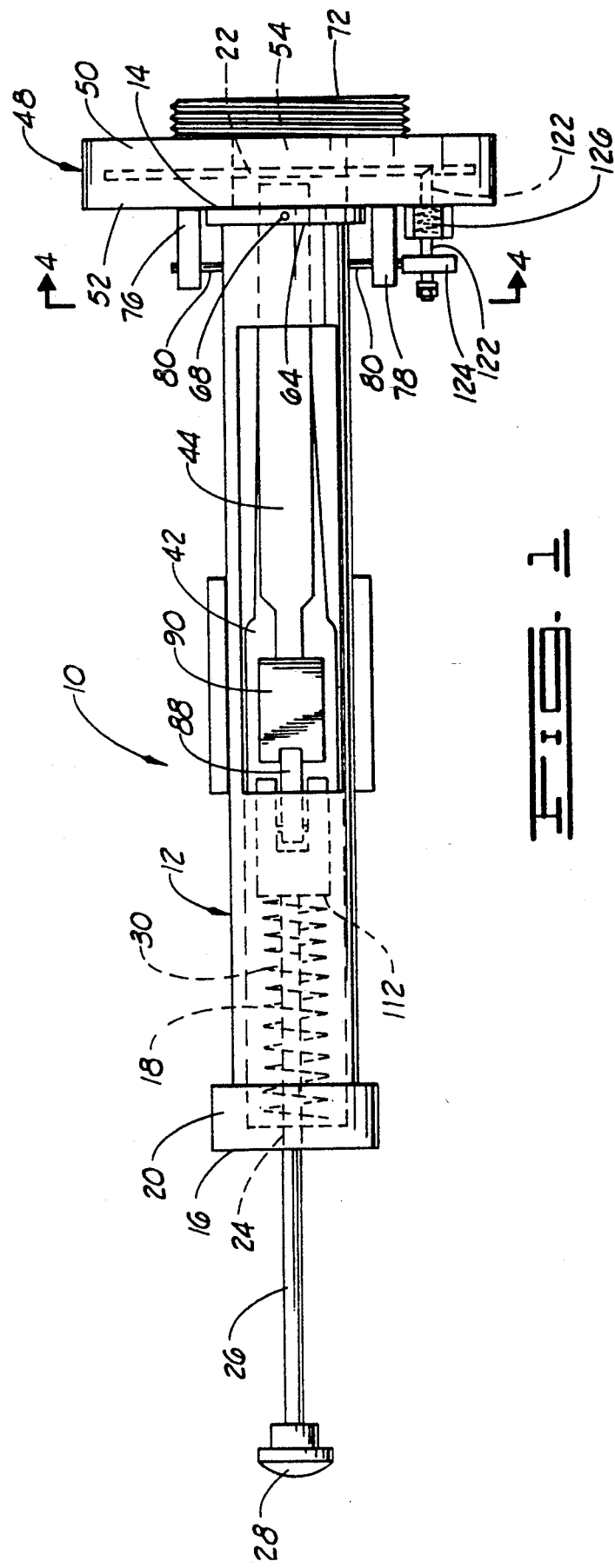
FIG. 1 is a top plan view of an instrument constructed in accordance with the present invention.
Figure 2:
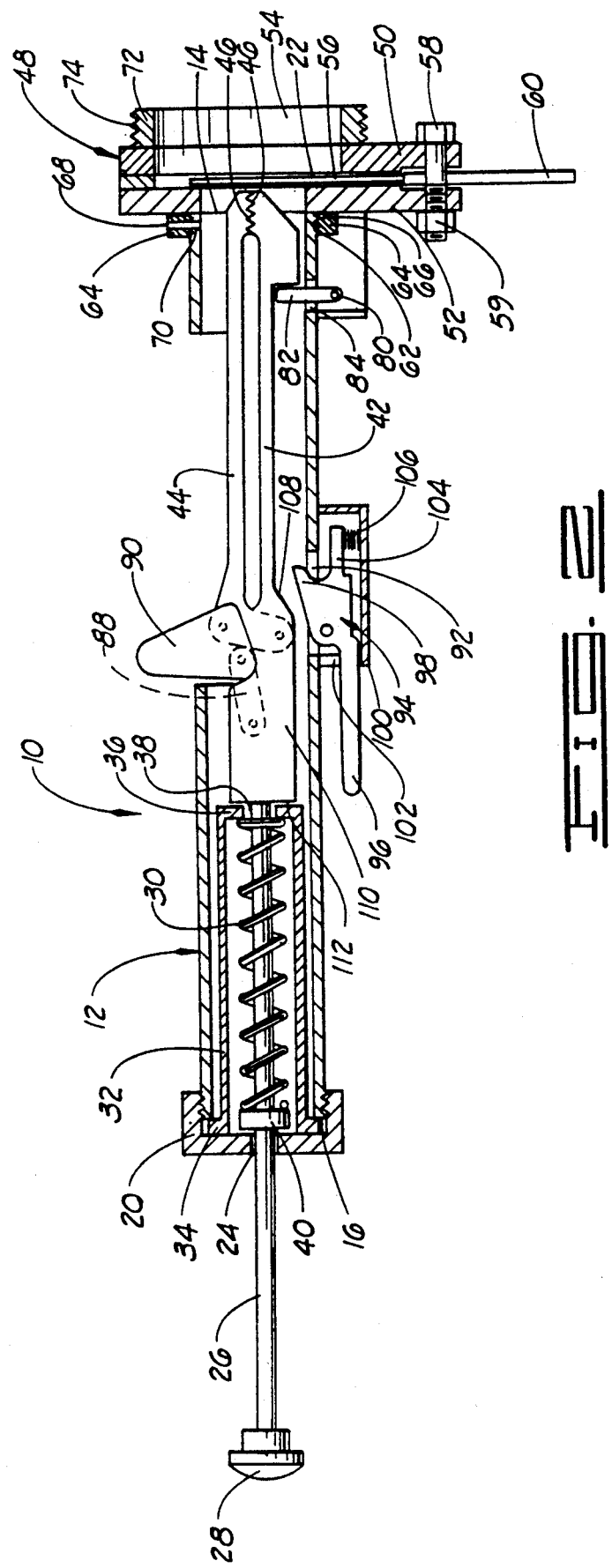
FIG. 2 is a partly sectional side elevation of the instrument of FIG. 1 with the forceps members in the rearward, released position.

Referring now to the drawings in general, and to FIGS. 1 and 2 in particular, shown therein and designated by the general reference number 10 is a scrotum incisor instrument constructed in accordance with the present invention.

The scrotum incisor instrument 10 includes a barrel 12 having a forward end 14 and a rearward end 16. A channel 18 extends from the rearward end 16 to the forward end 14 of the barrel 12. At the rearward end 16, an end cap 20 encloses the channel 18. At the forward end 14, the channel 18 is open to a cutting area 22 extending across the channel 18.

The end cap 20 has a rod slot 24 therethrough and a rod 26 extends through the rod slot 24 and into the channel 18. The rearward end of the rod 26 is typically fitted with a knob 28. A rod spring 30 is positioned around the rod 26 to bias the rod 26 in the rearward, or released position, shown in FIGS. 1 and 2.

As best shown in FIG. 2, the rod spring 30 is contained within a rod spring receptacle 32 inside the channel 18 of the barrel 12. The rearward end of the rod spring receptacle 32 includes an outward collar 34 which is positioned between the end cap 20 and the rearward end of the barrel 12 to secure the rod spring receptacle 32 in the channel 18 of the barrel 12.

The forward end of the rod spring receptacle 32 has an inward collar 36 which prevents the rod spring 30 from traveling out of the rod spring receptacle 32 in the forward direction. The inward collar 36 forms a rod opening 38 in the forward end of the rod spring receptacle 32. The rod opening 38 of the rod spring receptacle 32 is large enough for the rod 26 to extend through it, but small enough to contain the rod spring 30.

Continuing to refer to FIG. 2, the rod 26 includes a rod spring stop 40 which extends from the rod 26 at a portion of the rod 26 inside the rod spring receptacle 32. The rod spring 30 is positioned in the rod spring receptacle 32 between the rod spring stop 40 of the rod 26 and the inward collar 36 of the rod spring receptacle 32. The rod spring stop 40 of the rod 26 engages the rear end of the rod spring 30 to compress the rod spring 30 when the rod 26 is pushed forward.

The forward end of the rod 26 is connected to a pair of forceps members 42 and 44. As best shown in FIG. 2, the forward end of each forceps member 42 and 44 has a clamping surface 46. The clamping surfaces 46 face one another in order to grasp a portion the scrotum of an animal between them. Typically, the clamping surfaces 46 are grooved to provide adequate gripping on the scrotum.

A knife housing 48 is attached to the forward end of the barrel 12. The knife housing 48 has a forward wall 50 and a rearward wall 52 with the cutting area 22 between the forward wall 50 and the rearward wall 52. A forceps opening 54 extends through the forward wall 50 and rearward wall 52 of the knife housing 48 and communicates with the channel 18 of the barrel 12. As shown in FIGS. 1 and 2, the cutting area 22 of the knife housing 48 is substantially perpendicular to the forceps opening 54 and the channel 18 of the barrel 12.

As best shown in FIG. 2, a knife 56 is located in the cutting area 22 of the knife housing 48 to pivot transversely across the open forward end of the channel 18.

The knife 56 is attached to the knife housing 48 with a pivot bolt 58 and nut 59 for easy removal of the knife 56 to clean, sharpen or replace the knife 56.

Continuing to refer to FIGS. 1 and 2, the forward end of the barrel 12 has a set of threads 62 and the rearward side of the knife housing 48 has a rear collar 64 which has threads 66 to mate with the threads 62 of the barrel 12. A lock slot 68 extends through the rear collar 64 and an aligning slot 70 extends through the barrel 12. A lock pin or screw (not shown) may be inserted into the lock slot 68 and aligning slot 70 to prevent the knife housing 48 from becoming unscrewed from the barrel 12 during use of the instrument 10.

A forward collar 72 is attached to the forward side of the knife housing 48. The forward collar 72 is provided with external threads 74 for attachment of optional collars (not shown) having different sized openings to the cutting area 22. Also a cover (not shown) may be threaded onto the forward collar 72 to enclose the forward end of the knife housing 48 when the instrument 10 is not in use.

As best illustrated by FIG. 1, a pair of blocks 76 and 78 are attached to the rear of the knife housing 48. One block 76 is on one side of the barrel 12 and the other block 78 is on the opposite side of the barrel 12. Each block 76 and 78 has a slot through it in order to receive a pivot bar 80. The pivot bar 80 extends underneath the barrel 12 and is journaled into the slots of the blocks 76 and 78.

With reference to FIG. 2, a pivot bar tab 82 is rigidly attached to a medial portion of the pivot bar 80. A tab opening 84 is provided through the barrel 12 into the channel 18. The pivot bar tab 82 extends from the pivot bar 80 through the tab opening 84 and into the channel 18 of the barrel 12.

The forward end of the lower forceps member 42 includes a forceps protrusion 86. The forceps protrusion 86 is located to engage the pivot bar tab 82 and rotate the pivot bar 80 during the rearmost movement of the lower forceps member 42.

The rod 26 is rigidly attached to the rearward end of the lower forceps member 42. The upper forceps member 44 is pivotally attached to the lower forceps member 42. In order to operatively connect the forceps members 42 and 44, a forceps link 88 and a forceps lever 90 are provided. The rearward end of the forceps link 88 is pivotally attached to the lower forceps member 42 and to a rear portion of the forceps lever 90. The forceps lever 90, in turn, is pivotally attached to an upper rear portion of the upper forceps member 44.

With continued reference to FIG. 2, the barrel 12 includes a trigger opening 92 into the channel 18. A trigger 94 is pivotally mounted to the barrel 12 and has a trigger handle 96 and a trigger actuator 98. The trigger actuator 98 is pivotable through the trigger opening 92 into the channel 18 of the barrel 12. The trigger 94 is typically enclosed in a trigger housing 100 attached to the barrel 12. The trigger housing 100 includes a trigger handle opening 102 and the trigger handle 96 extends through and protrudes from the trigger handle opening 102. The trigger 94 also includes a trigger arm 104 which is positioned within the trigger housing 100. A trigger spring 106 is located between the trigger housing 100 and the trigger arm 104 to bias the trigger actuator 98 through the trigger opening 92 and into the channel 18 of the barrel 12.

With continued reference to FIG. 2, the lower forceps member 42 has an intermediate curved portion 108 leading to an enlarged rearward section 110 of the lower forceps member 42. The curved portion 108 and enlarged rearward section 110 of the lower forceps member 42 engage the trigger actuator 98 to overcome the bias of the trigger spring 106 as the forceps member 42 is moved forward. When the rearward end 112 of the forceps member 42 is forward of the trigger actuator 98, the bias of the trigger spring 106 urges the trigger actuator 98 into engagement with the rearward end 112 of the lower forceps member 42. Thus the rearward end 112 of the forceps member 42 acts as a trigger stop for the trigger 94 and the forceps members 42 and 44 are held in the forward, or cocked position, by the bias of the trigger spring 106 and the engagement of the trigger actuator 98 with the rearward end 112 of the forceps member 42.

Turning now to FIGS. 3 through 5, the cocked and released positions of the knife 56 are described in detail. As previously described, the knife 56 is attached to the knife housing 48 by the pivot bolt 58 and nut 59 to pivot in the cutting area 22 in front of the forward end of the channel 18. A knife spring 114 is provided to bias the knife 56 in the released position. One end of the knife spring 114 is attached to the knife 56 and the other end of the knife spring 114 is attached to the knife housing 48.

The knife 56 has a cutting edge 116, a knife handle 60 and a knife slot 118. The rear wall 52 of the knife housing 48 includes a knife housing slot 120 and a latch member 122 is biased to extend forwardly through the knife housing slot 120. As illustrated by FIG. 5, the knife slot 118 and the knife housing slot 120 are aligned and the latch member 122 extends through the knife housing slot 120 and into the knife slot 118 when the knife 56 is in the cocked position. It should be appreciated that the knife spring 114 is stretched beyond its normal length when the knife 56 is cocked.

Referring now to FIG. 4, the structure correlating the rotation of the pivot bar 80 with movement of the latch member 122 is described. The pivot bar tab 80, journaled through the blocks 76 and 78, is free to pivot while being supported by the blocks 76 and 78. The pivot bar tab 82 is rigidly attached to the pivot bar 80 between the blocks 76 and 78 to extend into the channel 18 of the barrel 12.

Outside the block 78 and beneath the latch member 122, a pivot bar link 124 connects the pivot bar 80 to the latch member 122. One end of the pivot bar link 124 is rigidly attached to the pivot bar 80 and the other end of the pivot bar link 124 is secured to the latch member 122. With this construction, the latch member 122 moves to the rear in response to the rearward movement of the pivot bar tab 82.

Referring back to FIG. 1, a latch spring 126 is located at the rear of the knife housing 48 to bias the latch member 122 toward a forward position. The forward end 128 of the latch member 122 is beveled so that the knife 56 overcomes the bias of the latch spring 126 to push the latch member 122 rearward as the knife 56 is pivoted into the cocked position.

Figure 6:
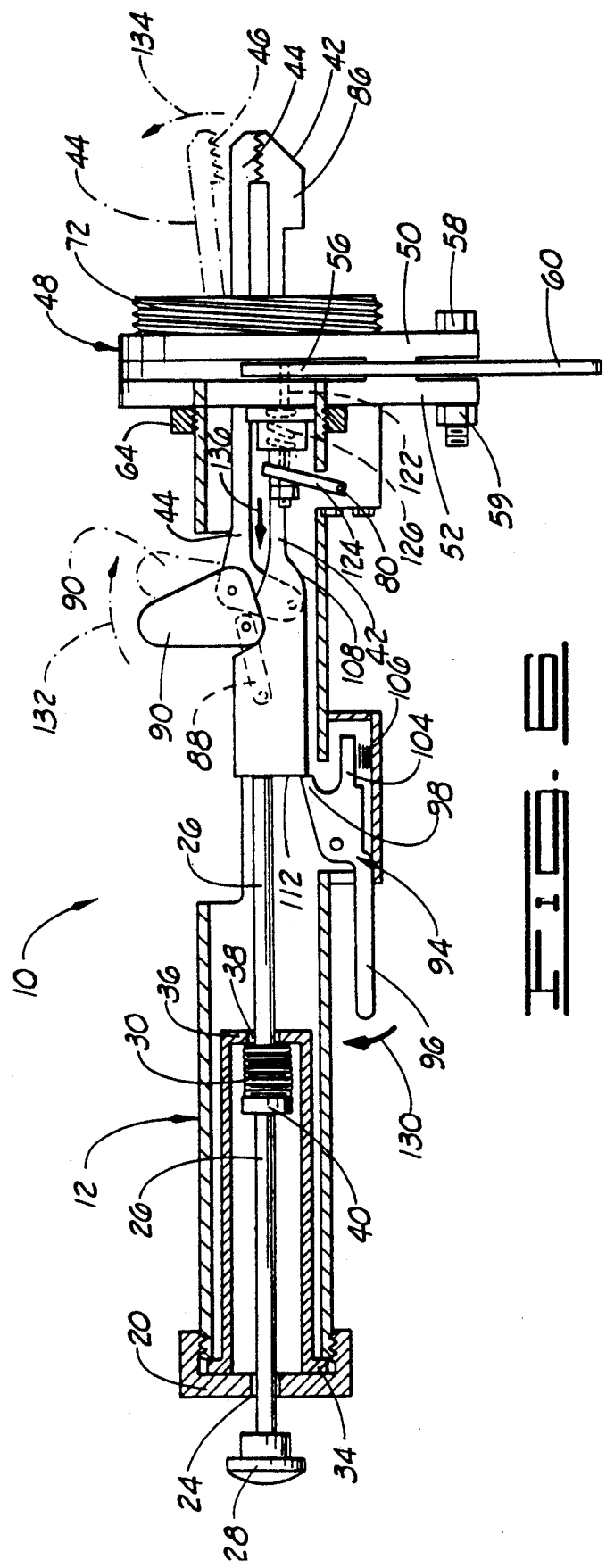
FIG. 6 is a partly sectional side view of the instrument of FIG. 1 with the forceps members in the cocked position and illustrating the movement of the trigger, the forceps lever and the forceps members.

With reference now to FIG. 6, the cocked position of the instrument 10 is illustrated. In the cocked position, the forceps members 42 and 44 are extended through the channel 18 to protrude through the knife housing 48. The knife 56 is cocked with the latch member 122 extending into the knife slot 118 to hold the knife 56 in the cocked position.

When the instrument 10 is in the cocked position, the rod spring 30 is compressed by the forward movement of the rod 26. The rod spring 30 is held in compression by the trigger actuator 98 engaging the rearward end 112 of the lower forceps member 42.

Operation

Use of the instrument 10 typically begins with the rod 26 and forceps members 42 and 44 in the rearward, or released, position as shown in FIG. 2. At this time, the knife 56 is also in the released position illustrated by FIG. 3.

Before applying the instrument 10 to the scrotum of an animal, the knife 56 and the rod 26 are cocked. First, the knife 56 is cocked. Using the knife handle 60, the knife 56 is pivoted to overcome the bias of the knife spring 114 until the latch member 122 extends into the knife slot 118. The beveled forward end 128 of the latch member 122 allows the knife 56 to push the latch member 122 rearward as the knife is pivoted into the cocked position. The bias of the latch spring 126 urges the latch member 122 into the knife slot 118 as the knife slot 118 becomes aligned with the slot 120 in the rear wall 52 of the knife housing 48. The cocked position of the knife 56 is illustrated by FIG. 5.

After the knife 56 is cocked, the rod 26 is pushed forward to overcome the bias of the rod spring 30 until the trigger actuator 98 engages the rearward end 112 of the lower forceps member 42. The bias of the trigger spring 106 urges the trigger actuator 98 into engagement with the rearward end 112 of the lower forceps member 42. The cocked position of the rod 26 is illustrated by FIG. 6.

Once the knife 56 and rod 26 are cocked, the instrument 10 is ready to be applied to the scrotum of an animal. With continued reference to FIG. 6, the application of the instrument to the scrotum of an animal is described. It should be understood that the knife 56 and rod 26 remain cocked until the trigger handle 96 is pivoted in the direction indicated by direction arrow 130 in FIG. 6.

The forceps members 42 and 44 are placed upon a portion of the animal's scrotum. The forceps members 42 and 44 are applied to the animal's scrotum by pushing the forceps lever 90 forward as indicated by direction arrow 132. As previously described, the forceps lever 90, the forceps link 88 and the forceps members 42 and 44 are operatively connected. Accordingly, the upper forceps member 44 moves to an open position, as indicated by direction arrow 134, in response to the forward movement of the forceps lever 90. The forward position of the forceps lever 90 and the open position of the forceps member 44 are shown in outline in FIG. 6.

With the forceps members 42 and 44 held open, a portion of the animal's scrotum is positioned between the clamping surfaces 46 of the forceps members 42 and 44. When the portion of the animal's scrotum to be incised is between the clamping surfaces 46 of the forceps members 42 and 44, the forceps lever 90 is released and the clamping surfaces 46 of the forceps members 42 and 44 grasp the portion of an animal's scrotum.

Once the portion of the animal's scrotum is grasped by the clamping surfaces 46 of the forceps members 42 and 44, the trigger handle 96 is pivoted in direction 130 to disengage the trigger actuator 98 from the rearward end 112 of the lower forceps member 42. When this occurs, the rod spring 30 is suddenly released from compression and drives the rod 26 and forceps members 42 and 44 rapidly rearward.

The rearward movement of the forceps members 42 and 44 draws the portion of the scrotum grasped by the clamping surfaces 46 of the forceps members 42 and 44 to the rear of the cutting area 22 of the knife housing 48. Near the end of the rearward movement of the forceps members 42 and 44, the forceps protrusion 86 of the lower forceps member 42 engages the pivot bar tab 82 of the pivot bar 80 to rotate the pivot bar 80. Because the pivot bar link 124 is rigidly attached to the pivot bar 80, the pivot bar link 124 moves rearward with the rotation of the pivot bar 80 as indicated by direction arrow 136 to overcome the bias of the latch spring 126 and to move the latch member 122 rearward.

The rearward movement of the latch member 122 removes the latch member 122 from the knife slot 118. No longer held by the latch member 122, the knife 56 pivots through the cutting area 22 of the knife housing 48 in response to the bias of the knife spring 114. The cutting edge 116 of the knife 56 incises the portion of the scrotum drawn into the cutting area 22 by the forceps members 42 and 44.

It should be appreciated that applying the forceps members 42 and 44 to the scrotum and pressing the trigger handle 96 may be performed in quick succession. It should also be noted that the knife housing 48 protects the operator of the instrument 10 from the cutting edge 116 of the knife 56 during use of the instrument 10.

Referring back to FIGS. 3 and 4, the knife 56 may be removed for cleaning, sharpening or replacement simply by unhooking the knife spring 114 and removing the nut 59 and pivot bolt 58. Similarly, the knife 56 is installed by bolting the knife 56 in the cutting area 22 of the knife housing 48 and attaching the knife spring 114 to the knife housing 48 and the knife 56.

Changes may be made in the combinations, operations and arrangements of the various parts and elements described herein without departing from the spirit and scope of the invention defined in the following claims.

What is claimed is:

1. An instrument for grasping and incising the scrotum of an animal, the instrument comprising:
    a barrel having a forward end, a rearward end and a channel extending from the forward end of the barrel to the rearward end of the barrel, the rearward end of the barrel having a rod slot extending into the channel and the forward end of the barrel having a cutting area communicating with the channel;
    a rod extending through the rod slot into the channel and having a first end protruding from the barrel through the rod slot and a second end disposed within the channel;
    a pair of forceps members connected to the second end of the rod, the forceps members having a rearward end and a forward end, the forward end of the forceps members including a pair of opposing clamping faces, the clamping faces being movable between an open position wherein the clamping faces are spaced apart and a clamped position wherein the clapping faces are proximate to one another and are adapted to grasp a portion of the scrotum;
    a knife pivotally attached to the barrel at the forward end of the barrel, the knife having a cutting edge and being positioned to pivot through the cutting area; and actuating means for thrusting the cutting edge of the knife through the cutting area in response to rearward movement of the rod far enough to draw the portion of the scrotum grasped by the forceps members into the channel rearward of the cutting area.

2. The instrument of claim 1 wherein the knife has a cocked position and a released position and wherein the actuating means further comprises:

a knife housing attached to the forward end of the barrel, the knife housing having a forward wall and a rearward wall, the forward and rearward walls defining the cutting area therebetween;

a knife spring having one end connected to the knife and another end connected to the knife housing, the knife spring biasing the knife in the released position;

latch means for releasably securing the knife in the cocked position when the knife is pivoted to overcome the bias of the knife spring; and trip means for releasing the latch means to allow the bias of the knife spring to pivot the knife from the cocked position to the released position;

wherein the pivot of the knife from the cocked position to the released position thrusts the cutting edge of the knife through the cutting area.

3. The instrument of claim 2 wherein the knife has a knife handle for grasping to pivot the knife from the released position into the cocked position.

4. The instrument of claim 2 wherein the barrel has a tab opening extending into the channel near the forward end of the barrel and wherein the trip means further comprises:

a pivot bar pivotally attached to the knife housing and extending across the barrel substantially perpendicular with the channel of the barrel, the pivot bar having a pivot tab protruding into the channel of the barrel;

a pivot link having one end attached to the pivot bar and another end attached to the latch means; and a forceps protrusion connected to one of the forceps members;

wherein the pivot link moves rearward to overcome the bias of the latch spring and remove the latch means from the knife slot in response to rotation of the pivot bar by contact of the forceps protrusion with the pivot tab of the pivot bar as the rod is moved rearward.

5. The instrument of claim 1 wherein the knife has a knife slot therethrough and wherein the actuating means further comprises:

a knife housing attached to the forward end of the barrel, the knife housing having a forward wall and a rearward wall, the forward and rearward walls defining the cutting area therebetween, the rearward wall having a knife housing slot therethrough aligning with the knife slot when the knife is in the cocked position;

a latch member journaled through the knife housing slot of the rearward wall; and a latch spring cooperating with the latch member to bias the latch member toward the forward wall of the knife housing;

wherein the latch member extends through the knife slot when the knife is in the cocked position to releasably secure the knife in the cocked position.

6. The instrument of claim 5 wherein the latch member has a beveled forward end.

7. The instrument of claim 5 wherein the knife housing is removable.

8. The instrument of claim 5 further comprising:

a front collar attached to the forward wall of the knife housing, the front collar being adapted for removable attachment of an optional collar.

9. The instrument of claim 1 wherein the knife is removable.

10. The instrument of claim 1 further comprising:

a forceps link pivotally connected to one of the forceps members;

a forceps lever pivotally connected to the other one of the forceps members and to the forceps link;

wherein the forceps members are movable between the open position and the clamped position in response to pivoting movement of the forceps lever.

11. The instrument of claim 10 wherein the forceps link and the forceps lever cooperate with the forceps members and one another to bias the forceps members in the clamped position.

12. The instrument of claim 1 wherein the rod is movable within said channel between a forward cocked position and a rearward released position.

13. The instrument of claim 12 further comprising:

a rod spring cooperating with the rod to bias the rod in the released position.

14. The instrument of claim 13 wherein the rod has a rod spring stop engaging the rod spring to hold the rod spring in a position forward of the rod spring stop.

15. The instrument of claim 13 further comprising:

a rod spring receptacle sized and shaped to receive the rod spring and secured within the channel toward the rearward end of the barrel, the spring receptacle having a rear end with a rear rod slot therethrough and a forward end with a forward rod slot, the forward end of the rod spring receptacle having an inward collar preventing movement of the rod spring out of the forward end of the rod spring receptacle.

16. The instrument of claim 15 further comprising:

an end cap removably attached to the rearward end of the barrel, the end cap having an end opening therethrough to receive the rod.

17. The instrument of claim 16 wherein the rearward end of the rod spring receptacle has an outward collar and wherein the rod spring receptacle is secured in the channel by positioning the outward collar of the rod spring receptacle between the rearward end of the barrel and the end cap.

18. The instrument of claim 12 further comprising:

trigger means for holding the rod in the cocked position and for releasing the rod for movement to the released position.

19. The instrument of claim 18 wherein the barrel has a trigger slot communicating with the channel and the trigger means further comprises:

a trigger operably connected to the barrel and extending through the trigger slot into the channel of the barrel; and a trigger stop attached to the rod;

wherein the trigger is operable to engage the trigger stop to hold the rod in the cocked position and to disengage the trigger stop to release the rod for movement of the rod to the released position.

20. The instrument of claim 19 wherein the trigger stop is the rearward end of one of the forceps members.

21. The instrument of claim 19 further comprising:

a trigger spring cooperating with the trigger to bias the trigger toward engagement with the trigger stop.

* * * * *